(12) United States Patent
Kofod et al.

(10) Patent No.: US 6,329,185 B1
(45) Date of Patent: Dec. 11, 2001

(54) ENZYME WITH GALACTANASE ACTIVITY

(75) Inventors: Lene Venke Kofod, Uggerløse; Markus Sakari Kauppinen, Copenhagen N; Lene Nonboe Andersen, Allerød; Ib Groth Clausen, Hilerød, all of (DK)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 09/129,033

(22) Filed: Aug. 4, 1998

Related U.S. Application Data

(63) Continuation of application No. PCT/DK97/00091, filed on Feb. 28, 1997.

(30) Foreign Application Priority Data

Mar. 1, 1996 (DK) .................................................. 0234/96

(51) Int. Cl.[7] .............................. C12P 21/06; C12N 9/00; C12N 9/24; C12N 9/26
(52) U.S. Cl. ..................... 435/201; 435/69.1; 435/183; 435/200; 435/202; 435/206; 435/209
(58) Field of Search .................................... 435/69.1, 183, 435/200, 202, 206, 209, 201

(56) References Cited

FOREIGN PATENT DOCUMENTS

WO 92/13945  8/1992  (WO) .

OTHER PUBLICATIONS

EMBL, Database Genbank/DDBJ, Swissprot Accession No. L334599, Jul. 6, 1994.

Chemical Abstracts, vol. 114, No. 21, May 27, 1991, p. 434.

Dialog Information Service, File 155, Medline, Dialog Accession No. 06649288, Medline Accession No. 90237010.

Araujo et al., Journal of Industrial Microbiology, vol. 6, pp. 171–178 (1990).

*Primary Examiner*—Rebecca E. Prouty
*Assistant Examiner*—Manjunath N. Rao
(74) *Attorney, Agent, or Firm*—Elias J. Lambiris

(57) ABSTRACT

The present invention relates to an enzyme with galactanase activity, a DNA construct encoding the enzyme, a method of producing the enzyme, an enzyme composition comprising the enzyme, and the use of the enzyme and enzyme composition for a number of industrial applications.

19 Claims, No Drawings

ENZYME WITH GALACTANASE ACTIVITY

CROSS-REFERENCE TO RELATED APPLICATIONS

This application is a continuation of PCT/DK97/00091 filed Feb. 28, 1997 and claims priority under 35 U.S.C. 119 of Danish application 0234/96 filed Mar. 1, 1996, the contents of which are fully incorporated herein by reference.

FIELD OF INVENTION

The present invention relates to an enzyme with galactanase activity, a DNA construct encoding the enzyme with galactanase activity, a method of producing the enzyme, an enzyme composition comprising said enzyme with galactanase activity, and the use of said enzyme and enzyme composition for a number of industrial applications.

BACKGROUND OF THE INVENTION

Galactans and arabinogalactans are present in most plants as components of pectic hairy regions. They are usually attached to O-4 of rhamnose residues in the rhamnogalacturonan backbone of the hairy region. The distribution and composition of the sidechains vary considerably between different cell types and physiological states, but in general about half of the rhamnosyl units in the rhamnogalacturonan regions have sidechains attached. The galactan sidechains are in most plants type 1 galactans, which are composed of β-1,4 linked galactopyranose with some branching points and a length of up to 60 saccharide units (DP60). Arabinofuranose residues or short arabinan oligomers can be attached to the galactan chain at the O-3 of the galactosyl unit, thus named arabinogalactan. Galactans (or arabinogalactans) have an important function in the primary cell wall, where they interact with other structural components of the cell wall such as xyloglucans or arabinoxylans. Thus they possibly serve to anchor the pectic matrix in the cell wall. Furthermore, they increase the hydration and waterbinding capacity and decrease inter-chain association between pectin polymers which is thought to be of importance for modulation of porosity and passive diffusion. (Carpita & Gibeaut, 1993, Plant J.,3, 1–30; O'Neill et al.,1990, Methods in Plant Biochemistry, 415–441; Selvendran, 1983, The Chemistry of Plant Cell Walls. Dietary Fibers; Hwang et al., Food Hydrocolloids, 7, 39–53; Fry, 1988, The growing Plant Cell Wall: Chemical and Metabolic Analysis).

b-1,4-galactanases (E.C.3.2.1.89) degrade galactans (and arabinogalactans) and have been purified from a variety of microbial sources (Nakano et al., 1985, Agric. Biol. Chem., 49, 3445–3454; Emi & Yamamoto, 1972, Agric. Biol. Chem., 36, 1945–1954; Araujo & Ward, 1990, J. Ind. Microbiol., 6, 171–178; Van De Vis et al., 1991, Carbohydr. Polym., 16, 167–187).

Even though a number of b-1,4-galactanases have been purified, only one has been cloned and DNA sequenced.

WO 92/13945 decribe cloning and DNA sequencing of a fungal b-1,4-galactanase (*Aspergillus aculeatus*)

SUMMARY OF THE INVENTION

According to the present invention, the inventors have now for the first time succeeded in isolating and characterizing a DNA sequence, from a Basidiomycota fungus, which encodes an enzyme exhibiting galactanase activity, thereby making it possible to prepare a mono-component galactanase composition.

Accordingly, in a first aspect the invention relates to a DNA construct comprising a DNA sequence encoding an enzyme exhibiting galactanase activity, which DNA sequence comprises (a) the galactanase encoding part of the DNA sequence cloned into plasmid pYES 2.0 present in *Escherichia coli* DSM 10355;

(b) the DNA sequence shown in positions 1–1026 in SEQ ID NO 1 or more preferably 55–1026 or its complementary strand;

(c) an analogue of the DNA sequence defined in (a) or (b) which is at least 70% homologous with said DNA sequence;

(d) a DNA sequence which hybridizes with the DNA sequence shown in positions 1–1026 in SEQ ID NO 1 at low stringency;

(e) a DNA sequence which, because of the degeneracy of the genetic code, does not hybridize with the sequences of (b) or (d), but which codes for a polypeptide having the same amino acid sequence as the polypeptide encoded by any of these DNA sequences; or (f) a DNA sequence which is a allelic form or fragment of the DNA sequences specified in (a), (b), (c), (d), or (e).

The full length DNA sequence encoding a galactanase has been derived from a strain of the filamentous fungus *Meripilus giganteus* and has been cloned into plasmid pYES 2.0 present in the *Escherichia coli* strain DSM No. 10355.

Said galactanase encoding DNA sequence harboured in *Escherichia coli* DSM 10355 is believed to have the same sequence as that presented in SEQ ID NO 1. Accordingly, whenever reference is made to the galactanase encoding part of the DNA sequence cloned into plasmid pYES 2.0 present in DSM 10355 such reference is also intended to include the galactanase encoding part of the DNA sequence presented in SEQ ID NO 1.

Accordingly, the terms "the galactanase encoding part of the DNA sequence cloned into plasmid pYES 2.0 present in DSM 10355" and "the galactanase encoding part of the DNA sequence presented in SEQ ID NO 1" may be used interchangeably.

In further aspects the invention provides an expression vector harbouring the DNA construct of the invention, a cell comprising said DNA construct or said expression vector and a method of producing an enzyme exhibiting galactanase activity, which method comprises culturing said cell under conditions permitting the production of the enzyme, and recovering the enzyme from the culture.

In a still further aspect the invention provides an isolated enzyme exhibiting galactanase activity selected from the group consisting of:

(a) a polypeptide encoded by the galactanase enzyme encoding part of the DNA sequence cloned into plasmid pYES 2.0 present in *Escherichia coli* DSM 10355;

(b) a polypeptide comprising an amino acid sequence as shown in positions 19–342 of SEQ ID NO 2;

(c) an analogue of the polypeptide defined in (a) or (b) which is at least 70% homologous with said polypeptide; and (d) an allelic form or fragment of (a), (b) or (c).

In a still further aspect, the present invention relates to the use of an enzyme or an enzyme composition of the invention for various industrial applications.

Finally the invention relates to an isolated substantially pure biological culture of the *Escherichia coli* strain DSM No. 10355 harbouring a galactanase encoding DNA sequence (the galactanase encoding part of the DNA sequence cloned into plasmid pYES 2.0 present in *Escherichia coli* DSM 10355) derived from a strain of the filamentous fungus *Meripilus giganteus*, or any mutant of said *E. coli* strain having retained the galactanase encoding capability; and to an isolated substantially pure biological culture of the filamentous fungus *Meripilus giganteus* CBS No. 521.95, from which the DNA sequence presented as SEQ ID No. 1 has been derived.

DEFINITIONS

Prior to discussing this invention in further detail, the following terms will first be defined.

"A DNA construct": The term "A DNA construct", refers to a DNA sequence cloned in accordance with standard cloning procedures used in genetic engineering to relocate a segment of DNA from its natural location to a different site where it will be reproduced. The cloning process involves excision and isolation of the desired DNA segment, insertion of the piece of DNA into the vector molecule and incorporation of the recombinant vector into a cell where multiple copies or clones of the DNA segment will be replicated.

The "DNA construct" of the invention may alternatively be termed "cloned DNA sequence" or "isolated DNA sequence".

"Obtained from": For the purpose of the present invention the term "obtained from" as used herein in connection with a specific microbial source, means that the enzyme is produced by the specific source, or by a cell in which a gene from the source have been inserted.

"An isolated polypeptide": As defined herein the term, "an isolated polypeptide" or "isolated galactanase", as used about the galactanase of the invention, is a galactanase or galactanase part which is at least about 20% pure, preferably at least about 40% pure, more preferably about 60% pure, even more preferably about 80% pure, most preferably about 90% pure, and even most preferably about 95% pure, as determined by SDS-PAGE. The term "isolated polypeptide" may alternatively be termed "purified polypeptide".

"Homologous impurities": As used herein the term "homologous impurities" means any impurity (e.g. another polypeptide than the enzyme of the invention) which originate from the homologous cell where the enzyme of the invention is originally obtained from. In the present invention the homologous cell may e.g. be a strain of *Meripilus giganteus*.

"Galactanase encoding part": As used herein the term "galactanase encoding part" used in connection with a DNA sequence means the region of the DNA sequence which corresponds to the region which is translated into a polypeptide sequence. In the DNA sequence shown in SEQ ID NO 1 it is the region between the first "ATG" start codon ("AUG" codon in mRNA) and the following stop codon ("TAA", "TAG" or "TGA"). In others words this is the translated polypeptide.

The translated polypeptide comprises, in addition to the mature sequence exhibiting galactanase activity, an N-terminal signal sequence. The signal sequence generally guides the secretion of the polypeptide. For further information see (Stryer, L., "Biochemistry" W.H., Freeman and Company/New York, ISBN 0-7167-1920-7).

In the present context the term "galactanase encoding part" is intended to cover the translated polypeptide and the mature part thereof.

"Galactanase" In the present context galactanase is defined according to the Enzyme classification (EC), as having the EC-number: 3.2.1.89.
Official Name:ARABINOGALACTAN ENDO-1,4-BETA-GALACTOSIDASE.

Alternative Name(s):
ENDO-1,4-BETA-GALACTANASE.
GALACTANASE.
ARABINOGALACTANASE.
Reaction catalysed:
ENDOHYDROLYSIS OF 1,4-BETA-D-GALACTOSIDIC LINKAGES IN ARABINO-GALACTANS.

DETAILED DESCRIPTION OF THE INVENTION

DNA Constructs

The present invention provides a DNA construct comprising a DNA sequence encoding an enzyme exhibiting galactanase activity, which DNA sequence comprises
(a) the galactanase encoding part of the DNA sequence cloned into plasmid pYES 2.0 present in *Escherichia coli* DSM 10355;
(b) the DNA sequence shown in positions 1–1026 in SEQ ID NO 1 or more preferably 55–1026 or its complementary strand;
(c) an analogue of the DNA sequence defined in (a) or (b) which is at least 70% homologous with said DNA sequence;
(d) a DNA sequence which hybridizes with the DNA sequence shown in positions 1–1026 in SEQ ID NO 1 at low stringency;
(e) a DNA sequence which, because of the degeneracy of the genetic code, does not hybridize with the sequences of b) or (d), but which codes for a polypeptide having the same amino acid sequence as the polypeptide encoded by any of these DNA sequences; or
(f) a DNA sequence which is a allelic form or fragment of the
DNA sequences specified in (a), (b), (c), (d), or (e).

It is presently believed that the galactanase encoding part of the DNA sequence cloned into plasmid PYES 2.0 present in DSM 10355 is identical to the galactanase encoding part of the DNA sequence presented in SEQ ID NO 1.

Accordingly, the terms "the galactanase encoding part of the DNA sequence cloned into plasmid pYES 2.0 present in DSM 10355" and "the galactanase encoding part of the DNA sequence presented in SEQ ID NO 1" may be used interchangeably.

The DNA sequence may be of genomic, cDNA, or synthetic origin or any combination thereof.

The present invention also encompasses a cloned DNA sequence which encodes an enzyme exhibiting galactanase activity having the amino acid sequence set forth as the mature part of SEQ ID NO 2 (i.e. pos. 19–342), which DNA sequence differs from SEQ ID NO 1 by virtue of the degeneracy of the genetic code.

The DNA sequence shown in SEQ ID NO 1 and/or an analogue DNA sequence of the invention may be obtained from a microorganism such as a bacteria, a yeast or a filamentous fungus. Preferably it is obtained from a filamentous fungus and examples of suitable ones are given in the section "Microbial sources" (vide infra).

Alternatively, the analogous sequence may be constructed on the basis of the DNA sequence presented as the galactanase encoding part of SEQ ID No. 1, e.g be a sub-sequence thereof, and/or by introduction of nucleotide substitutions which do not give rise to another amino acid sequence of the galactanase encoded by the DNA sequence, but which corresponds to the codon usage of the host organism intended for production of the enzyme, or by introduction of nucleotide substitutions which may give rise to a different amino acid sequence.

When carrying out nucleotide substitutions, amino acid changes are preferably of a minor nature, that is conservative amino acid substitutions that do not significantly affect the folding or activity of the protein, small deletions, typically of one to about 30 amino acids; small amino- or carboxyl-terminal extensions, such as an amino-terminal methionine residue, a small linker peptide of up to about 20–25 residues, or a small extension that facilitates purification, such as a poly-histidine tract, an antigenic epitope or a binding domain.

Examples of conservative substitutions are within the group of basic amino acids (such as arginine, lysine, histidine), acidic amino acids (such as glutamic acid and aspartic acid), polar amino acids (such as glutamine and asparagine), hydrophobic amino acids (such as leucine, isoleucine, valine), aromatic amino acids (such as phenylalanine, tryptophan, tyrosine) and small amino acids (such as glycine, alanine, serine, threonine, methionine). For a general description of nucleotide substitution, see e.g. Ford et al., (1991), Protein Expression and Purification 2, 95–107.

It will be apparent to persons skilled in the art that such substitutions can be made outside the regions critical to the function of the molecule and still result in an active polypeptide. Amino acids essential to the activity of the polypeptide encoded by the DNA construct of the invention, and therefore preferably not subject to substitution, may be identified according to procedures known in the art, such as site-directed mutagenesis or alanine-scanning mutagenesis (cf. e.g. Cunningham and Wells, (1989), Science 244, 1081–1085). In the latter technique mutations are introduced at every residue in the molecule, and the resultant mutant molecules are tested for biological (i.e. galactanase) activity to identify amino acid residues that are critical to the activity of the molecule. Sites of substrate-enzyme interaction can also be determined by analysis of crystal structure as determined by such techniques as nuclear magnetic resonance analysis, crystallography or photoaffinity labelling (cf. e.g. de Vos et al., (1992), Science 255, 306–312; Smith et al., (1992), J. Mol. Biol. 224, 899–904; Wlodaver et al., (1992), FEBS Lett. 309, 59–64).

The DNA sequence homology referred to in (c) above is determined as the degree of identity between two sequences indicating a derivation of the first sequence from the second. The homology may suitably be determined by means of computer programs known in the art, such as GAP provided in the GCG program package (Program Manual for the Wisconsin Package, Version 8, August 1994, Genetics Computer Group, 575 Science Drive, Madison, Wis., USA 53711) (Needleman, S. B. and Wunsch, C. D., (1970), Journal of Molecular Biology, 48, 443–453). Using GAP with the following settings for DNA sequence comparison: GAP creation penalty of 5.0 and GAP extension penalty of 0.3, the coding region of the analogous DNA sequences referred to above exhibits a degree of identity preferably of at least 70%, more preferably at least 80%, more preferably at least 90%, more preferably at least 95%, more preferably at least 97% with the galactanase encoding part of the DNA sequence shown in SEQ ID No. 1.

The hybridization conditions referred to above to define an analogous DNA sequence as defined in (d) above which hybridizes to the galactanase encoding part of the DNA sequence shown in SEQ ID NO 1, i.e. nucleotides 1–1026, under at least low stringency conditions, but preferably at medium or high stringency conditions are as described in detail below.

Suitable experimental conditions for determining hybridization at low, medium, or high stringency between a nucleotide probe and a homologous DNA or RNA sequence involves pre-soaking of the filter containing the DNA fragments or RNA to hybridize in 5×SSC (Sodium chloride/Sodium citrate, Sambrook et al. 1989) for 10 min, and prehybridization of the filter in a solution of 5×SSC, 5×Denhardt's solution (Sambrook et al. 1989), 0.5% SDS and 100 µg/ml of denatured sonicated salmon sperm DNA (Sambrook et al. 1989), followed by hybridization in the same solution containing a concentration of 10 ng/ml of a random-primed (Feinberg, A. P. and Vogelstein, B. (1983) Anal. Biochem. 132:6–13), $^{32}$P-dCTP-labeled (specific activity >1×10$^9$ cpm/µg ) probe for 12 hours at ca. 45° C. The filter is then washed twice for 30 minutes in 2×SSC, 0.5% SDS at least 55° C. (low stringency), more preferably at least 60° C (medium stringency), still more preferably at least 65° C. (medium/high stringency), even more preferably at least 70° C. (high stringency), and even more preferably at least 75° C. (very high stringency).

Molecules to which the oligonucleotide probe hybridizes under these conditions are detected using a x-ray film.

The polypeptide homology referred to above (property (c)) of the polypeptide of the invention is determined as the degree of identity between two sequences indicating a derivation of the first sequence from the second. The homology may suitably be determined by means of computer programs known in the art such as GAP provided in the GCG program package (Program Manual for the Wisconsin Package, Version 8, August 1994, Genetics Computer Group, 575 Science Drive, Madison, Wis., USA 53711) (Needleman, S. B. and Wunsch, C. D., (1970), Journal of Molecular Biology, 48, 443–453). Using GAP with the following settings for polypeptide sequence comparison: GAP creation penalty of 3.0 and GAP extension penalty of 0.1, the mature part of a polypeptide encoded by an analogous DNA sequence of the invention exhibits a degree of identity preferably of at least 70%, more preferably at least 80%, more preferably at least 90%, more preferably at least 95%, and especially at least 97% with the mature part of the amino acid sequence shown in SEQ ID NO 2, i.e. position 19–342 in SEQ ID NO 2.

The present invention is also directed to galactanase variants which have an amino acid sequence which differs by no more than three amino acids, preferably by no more than two amino acids, and more preferably by no more than one amino acid from the mature part of the amino acid sequence set forth in SEQ ID NO 2.

The DNA sequence encoding a galactanase of the invention can be isolated from the strain *Escherichia coli* DSM No. 10355 using standard methods e.g. as described by Sambrook et al., (1989), Molecular Cloning: A Laboratory Manual. Cold Spring Harbor Lab.; Cold Spring Harbor, N.Y.

The DNA sequence encoding an enzyme exhibiting galactanase activity of the invention can also be isolated by any general method involving cloning, in suitable vectors, a cDNA library from any organism expected to produce the galactanase of interest, transforming suitable yeast host cells with said vectors, culturing the host cells under suitable conditions to express any enzyme of interest encoded by a clone in the cDNA library, screening for positive clones by determining any galactanase activity of the enzyme produced by such clones, and isolating the enzyme encoding DNA from such clones.

A general isolation method has been disclosed in WO 93/11249 or WO 94/14953, the contents of which are hereby incorporated by reference. A more detailed description of the screening method is given in Example 1 below.

Alternatively, the DNA encoding a galactanase of the invention may, in accordance with well-known procedures, conveniently be isolated from a suitable source, such as any of the below mentioned organisms, by use of synthetic oligonucleotide probes prepared on the basis of a DNA sequence disclosed herein. For instance, a suitable oligonucleotide probe may be prepared on the basis of the galactanase encoding part of the nucleotide sequences presented as SEQ ID No. 1 or any suitable subsequence thereof, or the basis of the amino acid sequence SEQ ID NO 2.

Microbial Sources

In a preferred embodiment, the DNA sequence encoding the galactanase is derived from a strain belonging to the Polyporaceae family, which according to the entrez browser NCBI taxonomy version 3,3, (updated 12.13.95) is a family within the order Aphyllophorales, which belong to the class of Hymenomycetes under the Basidiomycota.

It is at present contemplated that a DNA sequence encoding an enzyme homologous to the enzyme of the invention, i.e. an analogous DNA sequence, may be obtained from other microorganisms. For instance, the DNA sequence may be derived by similarly screening a cDNA library of another microorganism, in particular a fungus, such as a strain of an Aspergillus sp., in particular a strain of *A. aculeatus* or *A. niger*, a strain of a Phytophthora sp., in particular a strain of *P. infestans, P. megasperma, P. cactorum* or a strain of a Talaromyces sp., in particular a strain of *T. byssochlamydoides, T. emersonii*, a strain of a Thermoascus sp., in particular a strain of *T. aurantiacus*, a strain of a Sporotrichum sp., in particular a strain of *S. celluphilum* or a strain of a Penicillium sp., in particular a strain of *P. citrinum, P. camembertii* or *P. roquefortii*.

An isolate of a strain of *Meripilus giganteus* from which an galactanase of the invention can be derived has been deposited by the inventors according to the Budapest Treaty on the International Recognition of the Deposit of Microorganisms for the Purposes of Patent Procedure at the Centraalbureau voor Schimmelcultures, P.O. Box 273, 3740 AG Baarn, The Netherlands, (CBS).

Deposit date: 04.07.95
Depositor's ref.: NN006040
CBS designation: *Meripilus giganteus* CBS No. 521.95

Further, the expression plasmid pYES 2.0 comprising the full length DNA sequence encoding the galactanase of the invention has been transformed into a strain of the *Escherichia coli* which was deposited by the inventors according to the Budapest Treaty on the International Recognition of the Deposit of Microorganisms for the Purposes of Patent Procedure at the Deutshe Sammlung von Mikroorganismen und Zellkulturen GmbH., Masheroder Weg 1b, D-38124 Raunschweig, Federal Republic of Germany, (DSM).

Deposit date: 06.12.95
Depositor's ref.: NN049142
DSM designation *Escherichia coli* DSM No. 10355

Expression Vectors

In another aspect, the invention provides a recombinant expression vector comprising the DNA construct of the invention.

The expression vector of the invention may be any expression vector that is conveniently subjected to recombinant DNA procedures, and the choice of vector will often depend on the host cell into which it is to be introduced. Thus, the vector may be an autonomously replicating vector, i.e. a vector which exists as an extrachromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated.

In the expression vector, the DNA sequence encoding the galactanase should be operably connected to a suitable promoter and terminator sequence. The promoter may be any DNA sequence which shows transcriptional activity in the host cell of choice and may be derived from genes encoding proteins either homologous or heterologous to the host cell. The procedures used to ligate the DNA sequences coding for the galactanase, the promoter and the terminator, respectively, and to insert them into suitable vectors are well known to persons skilled in the art (cf., for instance, Sambrook et al., (1989), Molecular Cloning. A Laboratory Manual, Cold Spring Harbor, N.Y.). Examples of suitable promoters for use in filamentous fungus host cells are, for instance, the ADH3 promoter (McKnight et al., *The EMBO J.* 4 (1985), 2093–2099) or the tpiA promoter. Examples of other useful promoters are those derived from the gene encoding *Aspergillus oryzae* TAKA amylase, *Rhizomucor miehei* aspartic proteinase, *Aspergillus niger* neutral a-amylase, *Aspergillus niger* acid stable a-amylase, *Aspergillus niger* or *Aspergillus awamori* glucoamylase (gluA), *Rhizomucor miehei* lipase, *Aspergillus oryzae* alkaline protease, *Aspergillus oryzae* triose phosphate isomerase or *Aspergillus nidulans* acetamidase.

Host Cells

In yet another aspect the invention provides a host cell comprising the DNA construct of the invention and/or the recombinant expression vector of the invention.

Preferably, the host cell of the invention is a eukaryotic cell, in particular a fungal cell such as a yeast or filamentous fungal cell. In particular, the cell may belong to a species of Trichoderma, preferably *Trichoderma harzianum* or *Trichoderma reesei*, or a species of Aspergillus, most preferably *Aspergillus oryzae* or *Aspergillus niger*, or a species of Fusarium, most preferably a Fusarium sp. having the identifying characteristic of Fusarium ATCC 20334, as further described in PCT/US/95/07743.

Fungal cells may be transformed by a process involving protoplast formation and transformation of the protoplasts followed by regeneration of the cell wall in a manner known per se. The use of Aspergillus as a host microorganism is described in EP 238 023 (Novo Nordisk A/S), the contents of which are hereby incorporated by reference. The host cell may also be a yeast cell, e.g. a strain of Saccharomyces, in particular *Saccharomyces cerevisae, Saccharomyces kluyveri* or *Saccharomyces uvarum*, a strain of Schizosaccharomyces sp., such as *Schizosaccharomyces pombe*, a strain of Hansenula sp., Pichia sp., Yarrowia sp., such as *Yarrowia lipolytica*, or Kluyveromyces sp., such as *Kluyveromyces lactis*.

Method of Producing Galactanase

The present invention provides a method of producing an isolated enzyme according to the invention, wherein a suitable host cell, which has been transformed with a DNA sequence encoding the enzyme, is cultured under conditions permitting the production of the enzyme, and the resulting enzyme is recovered from the culture.

When an expression vector comprising a DNA sequence encoding the enzyme is transformed into a heterologous host cell it is possible to enable heterologous recombinant production of the enzyme of the invention.

Thereby it is possible to make a highly purified galactanase composition, characterized in being free from homologous impurities.

In the present invention the homologous host cell may be a strain of *Meripilus giganteus*.

The medium used to culture the transformed host cells may be any conventional medium suitable for growing the host cells in question. The expressed galactanase may conveniently be secreted into the culture medium and may be recovered therefrom by well-known procedures including separating the cells from the medium by centrifugation or filtration, precipitating proteinaceous components of the medium by means of a salt such as ammonium sulphate, followed by chromatographic procedures such as ion exchange chromatography, affinity chromatography, or the like.

Enzyme Compositions

In a still further aspect, the present invention relates to an enzyme composition useful for the degradation of plant cell wall components, said composition being enriched in an enzyme exhibiting galactanase activity as described above. In this manner a boosting of the cell wall degrading ability of the enzyme composition can be obtained.

The enzyme composition having been enriched with an enzyme of the invention may e.g. be an enzyme composition comprising multiple enzymatic activities, in particular an enzyme composition comprising multiple plant cell wall degrading enzymes such as Biofeed+®, Energex®, Viscozym®, Pectinex®, Pectinex Ultra SP®, Celluclast or Celluzyme (all available from Novo Nordisk A/S.

In the present context, the term "enriched" is intended to indicate that the galactanase activity of the enzyme composition has been increased, e.g. with an enrichment factor of 1.1, conveniently due to addition of an enzyme of the invention prepared by the method described above.

The enzyme composition of the invention may, in addition to a galactanase of the invention, contain one or more other enzymes, for instance those with, xylanolytic, or pectinolytic activities such as a-arabinosidase, a-glucuronisidase, phytase, xylan acetyl esterase, arabinanase, rhamnogalacturonase, pectin acetylesterase, galactanase, polygalacturonase, pectin lyase, pectate lyase, glucanase, pectin methylesterase, laccase, or oxidoreductase. The additional enzyme(s) may be producible by means of a microorganism belonging to the genus Aspergillus, preferably *Aspergillus niger, Aspergillus aculeatus, Aspergillus awamori* or *Aspergillus oryzae*, or Trichoderma, or *Humicola insolens*.

Alternatively, the enzyme composition enriched in an enzyme exhibiting galactanase activity may be one which comprises an enzyme of the invention as the major enzymatic component, e.g. a mono-component enzyme composition.

The enzyme composition may be prepared in accordance with methods known in the art and may be in the form of a liquid or a dry composition. For instance, the enzyme composition may be in the form of a granulate or a microgranulate. The enzyme to be included in the composition may be stabilized in accordance with methods known in the art.

Examples are given below of preferred uses of the enzyme composition of the invention. The dosage of the enzyme composition of the invention and other conditions under which the composition is used may be determined on the basis of methods known in the art.

The enzyme composition according to the invention may be useful for at least one of the following purposes.

Degradation or Modification of Plant Material

The enzyme composition according to the invention is preferably used as an agent for degradation or modification of plant cell walls or any galactan-containing material originating from plant cells walls due to the high plant cell wall degrading activity of the galactanase of the invention.

The galactanase of the invention hydrolyse b-1,4 linkages in galactanss. Galactans are polysaccharides having a backbone composed of b-1,4 linked galactose. The backbone may have sidebranches such as arabinose. The composition and number of sidebranches vary according to the source of the galactan. (Stephen, A. M., 1983, ch. 3 in The Polysaccharides, Vol 2, Ed. Aspinall, G. O.).

The degradation of galactan by galactanases is facilitated by full or partial removal of the sidebranches. Arabinose sidegroups can be removed by a mild acid treatment or by alpha-arabinosidases. The oligomers with are released by the galactanase or by a combination of galactanases and sidebranch-hydrolysing enzymes as mentioned above can be further degraded to free galactose by beta-galactosidases.

The galactanase of the present invention can be used without other pectinolytic or hemicellulytic enzymes or with limited activity of other pectinolytic or hemicellulytic enzymes to degrade galactans for production of oligosaccharides. The oligosaccharides may be used as bulking agents, like arabinogalactan oligosaccharides released from soy cell wall material, or of more or less purified arabinogalactans from plant material.

The galactanase of the present invention can be used in combination with other pectinolytic or hemicellulytic enzymes to degrade galactans to galactose and other monosaccharides.

The galactanase of the present invention may be used alone or together with other enzymes like glucanases, pectinases and/or hemicellulases to improve the extraction of oil from oil-rich plant material, like soy-bean oil from soy-beans, olive-oil from olives or rapeseed-oil from rape-seed or sunflower oil from sunflower.

The galactanase of the present invention may be used for separation of components of plant cell materials. Of particular interest is the separation of sugar or starch rich plant material into components of considerable commercial interest (like sucrose from sugar beet or starch from potato) and components of low interest (like pulp or hull fractions). Also, of particular interest is the separation of protein-rich or oil-rich crops into valuable protein and oil and invaluable hull fractions. The separation process may be performed by use of methods known in the art.

The galactanase of the invention may also be used in the preparation of fruit or vegetable juice in order to increase yield, and in the enzymatic hydrolysis of various plant cell wall-derived materials or waste materials, e.g. from wine or juice production, or agricultural residues such as vegetable hulls, bean hulls, sugar beet pulp, olive pulp, potato pulp, and the like.

The plant material may be degraded in order to improve different kinds of processing, facilitate purification or extraction of other component than the galactans like purification of pectins from citrus, improve the feed value, decrease the water binding capacity, improve the degradability in waste water plants, improve the conversion of plant material to ensilage, etc.

By means of an enzyme preparation of the invention it is possible to regulate the consistency and appearence of processed fruit or vegetables. The consistency and appearence has been shown to be a product of the actual combination of enzymes used for processing, i.e. the specificity of the enzymes with which the galactanase of the invention is combined. Examples include the production of clear juice e.g. from apples, pears or berries; cloud stable juice e.g. from apples, pears, berries, citrus or tomatoes; and purees e.g. from carrots and tomatoes.

The galactanase of the invention may be used in modifying the viscosity of plant cell wall derived material. For instance, the galactanase may be used to reduce the viscosity of feed which contain galactan and to promote processing of viscous galactan containing material. The viscosity reduction may be obtained by treating the galactan containing plant material with an enyme preparation of the invention under suitable conditions for full or partial degradation of the galactan containing material.

The galactanase can be used e.g. in combination with other enzymes for the removal of pectic substances from plant fibres. This removal is essential e.g. in the production of textile fibres or other cellulosic materials. For this purpose plant fibre material is treated with a suitable amount of the galactanase of the invention under suitable conditions for obtaining full or partial degradation of pectic substances associated with the plant fibre material.

Animal Feed Additive

Galactanases of the present invention may be used for modification of animal feed and may exert their effect either in vitro (by modifying components of the feed) or in vivo. The galactanase is particularly suited for addition to animal feed compositions containing high amounts of arabinogalactans or galactans, e.g. Feed containing plant material from soy bean, rape seed, lupin etc. When added to the feed the galactanase significantly improves the in vivo breakdown of plant cell wall material, whereby a better utilization of the plant nutrients by the animal is achieved. Thereby, the growth rate and/or feed conversion ratio (i.e. the weight of ingested feed relative to weight gain) of the animal is improved. For example the indigestible galactan is degraded by galactanase, e.g. in combination with β-galactosidase, to galactose or galactooligomers which are digestible by the animal and thus contribute to the available energy of the feed. Also, by the degradation of galactan the galactanase may improve the digestibility and uptake of non-carbohydrate feed constituents such as protein, fat and minerals.

For further description reference is made to PCT/DK 96/00443 and a working example herein.

Wine and Juice Processing

An enzyme preparation of the invention may be used for depectinization and viscosity reduction in vegetable or fruit juice, especially in apple or pear juice. This may be accomplished by treating the fruit or vegetable juice with an enzyme preparation of the invention in an amount effective for degrading pectin-containing material contained in the fruit or vegetable juice.

The enzyme preparation may be used in the treatment of mash from fruits and vegetables in order to improve the extractability or degradability of the mash. For instance, the enzyme preparation may be used in the treatment of mash from apples and pears for juice production, and in the mash treatment of grapes for wine production Advantage of Monocomponent Galactanase From the foregoing it will be apparent that the galactanase of the invention may be produced as a single component enzyme preparation essentially free from other enzyme activies such as pectin methylesterase and other pectinolytic enzymes normally found to be present in commercially available galactanase containing pectinolytic, hemicellulolytic or cellulolytic enzyme preparations.

For this reason the use of the galactanase of the invention is especially advantageous for purposes in which the action of such other enzyme activities are undesirable. Examples include the production of cloud stable juices and the production of purees. In these productions the presence of, e.g. pectin methyl esterase normally found as a sideactivity in conventional pectinolytic enzyme preparations results in a decreased stability of the cloud in cloud stable juice or causes syneresis in puree.

Furthermore, due to its substantial purity the galactanase of the invention can be used to modify pectin in such a way that only the parts of the pectin which contain galactan will be degraded. If conventional pectinolytic activities were present a more extensive degradation of the pectin would be obtained with a resulting reduction in the viscosifying or gelling ability of the pectin.

Finally, the substantially pure galactanase can be used to selectively release galactose and galactooligomers from plant material used for feed. Galactose is readily digested by animals. Conventional pectinolytic or hemicellulolytic enzyme preparations with galactanase activity in addition to the galactanase contain a mixture of endo- and exo-enzymes which produce, e.g. xylose and galacturonic acid which are undesirable in feed.

The invention is described in further detail in the following examples which are not in any way intended to limit the scope of the invention as claimed.

Materials and Methods

Deposited Organisms

*Meripilus giganteus* CBS No. 521.95 comprises the galactanase encoding DNA sequence of the invention.

*Escherichia coli* DSM 10355 containing the plasmid comprising the full length DNA sequence, coding for the galactanase of the invention, in the shuttle vector pYES 2.0.

Other Strains

Yeast strain: The *Saccharomyces cerevisiae* strain used was W3124 (MATa; ura 3-52; leu 2–3, 112; his 3-D200; pep 4-1137; prc1::HIS3; prb1:: LEU2; cir+).

*E. Coli* strain: DH5a (Life Technologies A/S, Roskilde, Denmark)

Plasmids

The Aspergillus expression vector pHD414 is a derivative of the plasmid p775 (described in EP 238 023). The construction of pHD414 is further described in WO 93/11249.

pYES 2.0 (Invitrogen) pA2G55 (See example 1)

General Molecular Biology Methods

Unless otherwise mentioned the DNA manipulations and transformations were performed using standard methods of molecular biology (Sambrook et al. (1989) Molecular cloning: A laboratory manual, Cold Spring Harbor lab., Cold Spring Harbor, N.Y.; Ausubel, F. M. et al. (eds.) "Current protocols in Molecular Biology". John Wiley and Sons, 1995; Harwood, C. R., and Cutting, S. M. (eds.) "Molecular Biological Methods for Bacillus". John Wiley and Sons, 1990).

Enzymes for DNA manipulations were used according to the specifications of the suppliers.

Enzymes for DNA Manipulations

Unless otherwise mentioned all enzymes for DNA manipulations, such as e.g. restiction endonucleases, ligases etc., are obtained from New England Biolabs, Inc.

Fermentation Procedure of *Meripilus giganteus* CBS No. 521.95 for mRNA Isolation

*Meripilus giganteus* CBS No. 521.95 was inoculated from a plate with outgrown mycelium into a shake flask containing 100 ml cellulose-containing medium PD liquid broth (24 g potato dextrose broth, Difco 0549, deionized water up to 1000 ml; autoclave (121° C. for 15–20 min)).

The culture was fermented at 26° C. for 5 days. The resulting culture broth was filtered through miracloth and the mycelium was frozen down in liquid nitrogen.

mRNA was isolated from mycelium from this culture as described in (H. Dalboege et al Mol. Gen. Genet (1994) 243:253–260.; WO 93/11249; WO 94/14953).

Extraction of total RNA is performed with guanidinium thiocyanate followed by ultracentrifugation through a 5.7 M CsCl cushion, and isolation of poly(A)$^+$RNA is carried out by oligo(dT)-cellulose affinity chromatography using the procedures described in WO 94/14953.

cDNA synthesis

Double-stranded cDNA is synthesized from 5 mg poly (A)$^+$ RNA by the RNase H method (Gubler and Hoffman (1983) Gene 25:263–269, Sambrook et al. (1989) Molecular cloning: A laboratory manual, Cold Spring Harbor lab., Cold Spring Harbor, N.Y.). The poly(A)$^+$ RNA (5 mg in 5 ml of DEPC-treated water) is heated at 70° C. for 8 min. in a pre-siliconized, RNase-free Eppendorph tube, quenched on ice and combined in a final volume of 50 ml with reverse transcriptase buffer (50 mM Tris-Cl, pH 8.3, 75 mM KCl, 3 mM MgCl$_2$, 10 mM DTT, Bethesda Research Laboratories) containing 1 mM of DATP, dGTP and dTTP and 0.5 mM 5-methyl-dCTP (Pharmacia), 40 units human placental ribonuclease inhibitor (RNasin, Promega), 1.45 mg of oligo(dT)$_{18}$-Not I primer (Pharmacia) and 1000 units SuperScript II RNase H reverse transcriptase (Bethesda Research Laboratories). First-strand cDNA is synthesized by incubating the reaction mixture at 45° C. for 1 hour. After synthesis, the mRNA:cDNA hybrid mixture is gelfiltrated through a MicroSpin S-400 HR (Pharmacia) spin column according to the manufacturer's instructions.

After the gelfiltration, the hybrids are diluted in 250 ml second strand buffer (20 mM Tris-Cl, pH 7.4, 90 mM KCl, 4.6 mM MgCl$_2$, 10 mM (NH$_4$)$_2$SO$_4$, 0.16 mM bNAD+) containing 200 mM of each dNTP, 60 units $E.\ coli$ DNA polymerase I (Pharmacia), 5.25 units RNase H (Promega) and 15 units $E.\ coli$ DNA ligase (Boehringer Mannheim). Second strand cDNA synthesis is performed by incubating the reaction tube at 16° C. for 2 hours and additional 15 min. at 25° C. The reaction is stopped by addition of EDTA to a final concentration of 20 mM followed by phenol and chloroform extractions.

Mung Bean Nuclease Treatment

The double-stranded cDNA is precipitated at −20° C. for 12 hours by addition of 2 vols 96% EtOH, 0.2 vol 10 M NH$_4$Ac, recovered by centrifugation, washed in 70% EtOH, dried and resuspended in 30 ml Mung bean nuclease buffer (30 mM NaAc, pH 4.6, 300 mM NaCl, 1 mM ZnSO$_4$, 0.35 mM DTT, 2% glycerol) containing 25 units Mung bean nuclease (Pharmacia). The single-stranded hair-pin DNA is clipped by incubating the reaction at 30° C. for 30 min., followed by addition of 70 ml 10 mM Tris-Cl, pH 7.5, 1 mM EDTA, phenol extraction and precipitation with 2 vols of 96% EtOH and 0.1 vol 3 M NaAc, pH 5.2 on ice for 30 min.

Blunt-ending with T4 DNA polymerase

The double-stranded cDNAs are recovered by centrifugation and blunt-ended in 30 ml T4 DNA polymerase buffer (20 mM Tris-acetate, pH 7.9, 10 mM MgAc, 50 mM KAc, 1 mM DTT) containing 0.5 mM of each dNTP and 5 units T4 DNA polymerase (New England Biolabs) by incubating the reaction mixture at 16° C. for 1 hour. The reaction is stopped by addition of EDTA to a final concentration of 20 mM, followed by phenol and chloroform extractions, and precipitation for 12 hours at −20° C. by adding 2 vols 96% EtOH and 0.1 vol 3 M NaAc pH 5.2.

Adaptor Ligation, Not I Digestion and Size Selection

After the fill-in reaction the cDNAs are recovered by centrifugation, washed in 70% EtOH and dried. The cDNA pellet is resuspended in 25 ml ligation buffer (30 mM Tris-Cl, pH 7.8, 10 mM MgCl$_2$, 10 mM DTT, 0.5 mM ATP) containing 2.5 mg non-palindromic BstXI adaptors (Invitrogen) and 30 units T4 ligase (Promega) and incubated at 16° C. for 12 hours. The reaction is stopped by heating at 65° C. for 20 min. and then cooling on ice for 5 min. The adapted cDNA is digested with Not I restriction enzyme by addition of 20 ml water, 5 ml 10×Not I restriction enzyme buffer (New England Biolabs) and 50 units Not I (New England Biolabs), followed by incubation for 2.5 hours at 37° C. The reaction is stopped by heating at 65° C. for 10 min. The cDNAs are size-fractionated by gel electrophoresis on a 0.8% SeaPlaque GTG low melting temperature agarose gel (FMC) in 1×TBE to separate unligated adaptors and small cDNAs. The cDNA is size-selected with a cut-off at 0.7 kb and rescued from the gel by use of b-Agarase (New England Biolabs) according to the manufacturer's instructions and precipitated for 12 hours at −20° C. by adding 2 vols 96% EtOH and 0.1 vol 3 M NaAc pH 5.2.

Construction of Libraries

The directional, size-selected cDNA is recovered by centrifugation, washed in 70% EtOH, dried and resuspended in 30 ml 10 mM Tris-Cl, pH 7.5, 1 mM EDTA. The cDNAs are desalted by gelfiltration through a MicroSpin S-300 HR (Pharmacia) spin column according to the manufacturer's instructions. Three test ligations are carried out in 10 ml ligation buffer (30 mM Tris-Cl, pH 7.8, 10 mM MgCl$_2$, 10 mM DTT, 0.5 mM ATP) containing 5 ml double-stranded cDNA (reaction tubes #1 and #2), 15 units T4 ligase (Promega) and 30 ng (tube #1), 40 ng (tube #2) and 40 ng (tube #3, the vector background control) of BstXI–NotI cleaved pYES 2.0 vector. The ligation reactions are performed by incubation at 16° C. for 12 hours, heating at 70° C. for 20 min. and addition of 10 ml water to each tube. 1 ml of each ligation mixture is electroporated into 40 ml electrocompetent $E.\ coli$ DH10B cells (Bethesda research Laboratories) as described (Sambrook et al. (1989) Molecular cloning: A laboratory manual, Cold Spring Harbor lab., Cold Spring Harbor, N.Y.). Using the optimal conditions a library is established in $E.\ coli$ consisting of pools. Each pool is made by spreading transformed $E.\ coli$ on LB+ampicillin agar plates giving 15.000–30.000 colonies/plate after incubation at 37° C. for 24 hours. 20 ml LB+ampicillin is added to the plate and the cells were suspended herein. The cell suspension is shaked in a 50 ml tube for 1 hour at 37° C. Plasmid DNA is isolated from the cells according to the manufacturer's instructions using QIAGEN plasmid kit and stored at −20° C.

1 ml aliquots of purified plasmid DNA (100 ng/ml) from individual pools are transformed into $S.\ cerevisiae$ W3124 by electroporation (Becker and Guarante (1991) Methods Enzymol. 194:182–187) and the transformants are plated on SC agar containing 2% glucose and incubated at 30° C.

Identification of Positive Clones

The tranformants is plated on SC agar containing 0.1% AZCL galactan (Megazyme, Australia) and 2% Galactose and incubated for 3–5 days at 30° C.

Galactanase positive colonies is identified as colonies surrounded by a blue halo.

Isolation of a cDNA Gene for Expression in Aspergillus

A galactanase-producing yeast colony is inoculated into 20 ml YPD broth in a 50 ml glass test tube. The tube is shaken for 2 days at 30° C. The cells are harvested by centrifugation for 10 min. at 3000 rpm.

DNA is isolated according to WO 94/14953 and dissolved in 50 ml water. The DNA is transformed into $E.\ coli$ by standard procedures. Plasmid DNA is isolated from $E.\ coli$ using standard procedures, and analyzed by restriction enzyme analysis. The cDNA insert is excised using appropriate restriction enzymes and ligated into an Aspergillus expression vector.

Transformation of *Aspergillus oryzae* or *Aspergillus niger*

Protoplasts may be prepared as described in WO 95/02043, p. 16, line 21—page 17, line 12, which is hereby incorporated by reference.

100 μl of protoplast suspension is mixed with 5–25 μg of the appropriate DNA in 10 μl of STC (1.2 M sorbitol, 10 mM Tris-HCl, pH =7.5, 10 mM $CaCl_2$). Protoplasts are mixed with the aspergillus expression vector of interest. The mixture is left at room temperature for 25 minutes. 0.2 ml of 60% PEG 4000 (BDH 29576), 10 mM $CaCl_2$ and 10 mM Tris-HCl, pH 7.5 is added and carefully mixed (twice) and finally 0.85 ml of the same solution is added and carefully mixed. The mixture is left at room temperature for 25 minutes, spun at 2500 g for 15 minutes and the pellet is resuspended in 2 ml of 1.2 M sorbitol. After one more sedimentation the protoplasts are spread on minimal plates (Cove, Biochem. Biophys. Acta 113 (1966) 51–56) containing 1.0 M sucrose, pH 7.0, 10 mM acetamide as nitrogen source and 20 mM CsCl to inhibit background growth. After incubation for 4–7 days at 37° C. spores are picked and spread for single colonies. This procedure is repeated and spores of a single colony after the second reisolation is stored as a defined transformant.

Test of *A. oryzae* Transformants

Each of the transformants are inoculated in 10 ml of YPM (cf. below) and propagated. After 2–5 days of incubation at 30° C., the supernatant is removed. The galactanase activity is identified by applying 10 μl supernatant to 4 mm diameter holes punched out in agar plates containing 0.2% AZCLÔgalactan (MegazymeÔ, Australia). Galactanase activity is then identified as a blue halo.

Fed Batch Fermentation

Fed batch fermentation was performed in a medium comprising maltodextrin as a carbon source, urea as a nitrogen source and yeast extract. The fed batch fermentation was performed by inoculating a shake flask culture of *A. oryzae* host cells in question into a medium comprising 3.5% of the carbon source and 0.5% of the nitrogen source. After 24 hours of cultivation at pH 7.0 and 34° C. The continuous supply of additional carbon and nitrogen sources were initiated. The carbon source was kept as the limiting factor and it was secured that oxygen was present in excess. The fed batch cultivation was continued for 4 days.

Isolation of the DNA Sequence Shown in SEQ ID No. 1

The galactanase encoding part of the DNA sequence shown in SEQ ID No. 1 coding for the galactanase of the invention can be obtained from the deposited organism *Escherichia coli* DSM 10355 by extraction of plasmid DNA by methods known in the art (Sambrook et al. (1989) Molecular cloning: A laboratory manual, Cold Spring Harbor lab., Cold Spring Harbor, N.Y.).

Media

YPD: 10 g yeast extract, 20 g peptone, $H_2O$ to 900 ml. Autoclaved, 100 ml 20% glucose (sterile filtered) added.

YPM: 10 g yeast extract, 20 g peptone, $H_2O$ to 900 ml. Autoclaved, 100 ml 20% maltodextrin (sterile filtered) added.

10×Basal salt: 75 g yeast nitrogen base, 113 g succinic acid, 68 g NaOH, $H_2O$ ad 1000 ml, sterile filtered.

SC-URA: 100 ml 10×Basal salt, 28 ml 20% casamino acids without vitamins, 10 ml 1% tryptophan, $H_2O$ ad 900 ml, autoclaved, 3.6 ml 5% threonine and 100 ml 20% glucose or 20% galactose added.

SC-agar: SC-URA, 20 g/l agar added.

SC-variant agar: 20 g agar, 20 ml 10×Basal salt, $H_2O$ ad 900 ml, autoclaved

AZCL galactan (Megazyme, Australia)

PEG 4000 (polyethylene glycol, molecular weight=4,000) (BDH, England)

EXAMPLES

Example 1

Cloning and Expression of a Galactanase from *Meripilus giganteus* CBS No. 521.95 mRNA was isolated from *Meripilus giganteus*, CBS No. 521.95, grown in cellulose-containing fermentation medium with agitation to ensure sufficient aeration. Mycelia were harvested after 3–5 days' growth, immediately frozen in liquid nitrogen and stored at −80° C. A library from *Meripilus giganteus*, CBS No. 521.95, consisting of approx. $9 \times 10^5$ individual clones was constructed in *E. coli* as described with a vector background of 1%. Plasmid DNA from some of the pools was transformed into yeast, and 50–100 plates containing 250–400 yeast colonies were obtained from each pool.

Galactanase-positive colonies were identified and isolated on SC-agar plates with the AZCL galactan assay. cDNA inserts were amplified directly from the yeast colonies and characterized as described in the Materials and Methods section above. The DNA sequence of the cDNA encoding the galactanase is shown in SEQ ID No. 1 and the corresponding amino acid sequence is shown in SEQ ID No. 2.

The cDNA is obtainable from the plasmid in DSM 10355.

Total DNA was isolated from a yeast colony and plasmid DNA was rescued by transformation of *E. coli* as described above. In order to express the galactanase in Aspergillus, the DNA was digested with appropriate restriction enzymes, size fractionated on gel, and a fragment corresponding to the galactanase gene was purified. The gene was subsequently ligated to pHD414, digested with appropriate restriction enzymes, resulting in the plasmid pA2G55.

After amplification of the DNA in *E. coli* the plasmid was transformed into *Aspergillus oryzae* as described above.

Test of *A. oryzae* Transformants

Each of the transformants were tested for enzyme activity as described above. Some of the transformants had galactanase activity which was significantly larger than the *Aspergillus oryzae* background. This demonstrates efficient expression of the galactanase in *Aspergillus oryzae*.

Example 2

A homology search with the galactanase of the invention against nucleotide and protein databases was performed. The homology search showed that the most related galactanase was a beta-1,4-galactanase from *Aspergillus aculeatus*.

According to the method described in the "DETAILED DESCRIPTION OF THE INVENTION" the DNA homology of the galactanase of the invention against most prior art galactanases was determined using the computer program GAP. The galactanase of the invention has only 56% DNA homology to the beta-1,4-galactanase from *Aspergillus aculeatus* (WO 92/13945. This show that the galactanase of the invention indeed is distant from any known galactanases.

Example 3

Purification of Recombinant Galactanase from *M. giganteus*

The culture supernatants from the fermentation of *Aspergillus oryzae* expressing the recombinant enzyme was centrifuged and filtered through a 0.2 μm filter to remove the mycelia, ultrafiltered in a Filtron casette (Minisette) with a 3 kDa membrane and at the same time the buffer was changed to 50 mM $H_3BO_3$, 5 mM DMG, 1 mM $CaCl_2$, pH 7.0. The resulting sample was loaded onto a 50 ml Pharmacia Q Sepharose HP anion exchange column equilibrated in 50 mM $H_3BO3_1$, 5 mM DMG, 1 mM $CaCl_2$, pH 7.0. After the sample was applied, the column was washed in 50 mM $H_3BO_3$, 5 mM DMG, 1 mM $CaCl_2$, pH 7.0 and bound proteins were eluted with a linear increasing NaCl gradient from 0 to 0.5M NaCl in 50 mM $H_3BO_3$, 5 mM DMG, 1 mM $CaCl_2$, pH 7.0. Fractions were tested for galactanase activity on AZCL-galactan and fractions containing the activity were pooled. All galactanase activity was in the wash fraction.

The pH in the wash fraction from the Q-sepharose column was adjusted to pH 4.5 with acetic acid and applied to a 50 ml Pharmacia S Sepharose HP column equilibrated in 10 mM $CH_3COOH$/NaOH, pH 4.5. After washing the column, bound protein was eluted with a linear increasing NaCl gradient from 0 to 250 mM NaCl in 10 mM $CH_3COOH$/NaOH, pH 4.5. All galactanase activity was present in a single peak and was eluted in a electrophoretically pure form.

Protein concentration is determined by use of the "Bio-Rad protein assay" in accordance with the Manufactures (Bio-Rad Laboratories GmbH) recommendations.

Example 4

Characterization of Recombinant Galactanase from *M. giganteus*

The Molecular weight and iso-electric point of the enzyme was determined as described in WO 94/21785.

The activity of the enzyme was measured either by the release of reducing sugars from lupin galactan (MegaZyme, Australia) or by the release of blue colour from AZCL-potato-galactan (MegaZyme, Australia).

0.5 ml 0.4% AZCL-potato-galactan was mixed with 0.5 ml 0.1M citrate/phosphate buffer of optimal pH and 10 µl of a suitably diluted enzyme solution was added. Incubations were carried out in Eppendorf Thermomixers for 15 minutes at 30° C. (if not otherwise specified) before heat-inactivation of the enzyme at 95° C. for 20 minutes. Enzyme incubations were carried out in triplicate and a blank was produced in which enzyme was added but immediately inactivated. After centrifugation the absorbance of the supernatant was measured in microtiter plates at 620 nm and the blank value was subtracted.

0.5% solutions of lupin galactan were made in 0.1M citrate/phosphate of the optimal pH (if not otherwise specified), 10 µl of suitably diluted enzyme solution was added to 1 ml of substrate and incubations were carried out at 30° C. for 15 minutes before heat-inactivation at 95° C. for 20 minutes. Reducing sugars were determined by reaction, in microtiter plates, with a PHBAH reagent comprising 0.15 g of para hydroxy benzoic acid hydrazide (Sigma H-9882), 0.50 g of potassium-sodium tartrate (Merck 8087) and 2% NaOH solution up to 10.0 ml. Results of blanks were subtracted. Galactose was used as a standard.

pH and temperature optimums were measured on AZCL-galactan. 0.1M citrate/phosphate buffers of pH (2.5, 3.0, 3.5, 4.0, 4.5, 5.0, 5.5, 6.0, 6.5, 7.0, 7.5, 8.0, 8.5, 9.0, 9.5, 10.0) were used for determination of pH optimum. In order to determine the temperature optimum, 0.1M citrate/phosphate buffers at optimal pH were used for reaction at different temperatures for 15 minutes.

Km and specific activity was found by carrying out incubations at lupin galactan concentrations (S) ranging from 0.025 to 1.0% and measure the reducing sugars produced, then calculate the reaction rate (v), picture S/v as a function of S, carry out linear regression analysis, finding the slope (=1/Vmax) and the intercept (Km/Vmax) and calculating Km and the specific activity (=Vmax/E), where E is the amount of enzyme added.

| Enzyme | *M. giganteus* |
|---|---|
| Mw | 35 kDa |
| pI | 5.9 |
| pH optimum | 5.5 |
| temperature optimum | 40° C. |
| Km (% galactan) | 0.4–0.8 |
| Specific activity (µmol/min/mg) | 5000–7000 |

Aminoterminal Sequence

Aminoterminal analysis was determined by using Edman degradation with Applied Biosystem equipment (ABI 473A protein sequencer, Applied Biosytem, USA) carried out as described by manufacturer.

N-terminal Sequence(s)

For the galactanase of the invention having the amino acid sequence shown in SEQ ID NO 2 the N-terminal sequence is:

N-terminal Leu-Thr-Tyr-Lys-Gly-Ala-

The N-terminal amino acid Leu is position 19 in SEQ ID NO 2. This indicates the mature galactanase enzyme of the invention starts at position 19 in SEQ ID No 2.

Consequently the mature sequence is from 19–342 in SEQ ID no 2.

Example 5

Apparent Metabolizable Energy

The effects of the galactanase enzyme of the invention (obtained as described in Example 3) on the nutritive value of basal diet were assessed using a classical apparent metabolisable energy (AME) assay to estimate the amount of dietary energy available to the bird. The AME study was conducted with an experimental basal diet containing sorghum (64%) and soya bean meal (30%).

Commercial broiler chickens (Ingham™ IM98) were raised from hatch to 24 days of age in a floor pen in a controlled-temperature shed. The birds were given commercial starter feed for 21 days then commercial finisher feed. The chickens were weighed in groups of five and transferred to 48 metabolism cages located in another room in the same shed. Experimental diets were fed for seven days (days 1–7). The first three days (days 1–3) enabled the chickens to adapt to the cages and the feeds. Feed intake was measured during this period. During the following four days (days 4–7) feed intake was measured and all excreta collected and dried. Moisture content of excreta collected on day 5 was determined by overnight drying at 90° C. Each diet were given to 25 birds.

Dry matter (DM) contents of samples of sorghum, pelleted feeds, and milled feeds were determined by overnight drying at 105° C. Gross energy (GE) values of excreta and milled feeds were measured with a Parr isoperibol bomb calorimeter. Nitrogen contents of feed and excreta samples were measured by Kjeltec methods of digestion, distillation and titration.

In this experiment galactanase was included at a dosage of 6.7 ml/kg feed, and the lactase (Sumilact™, Lot. No. 40303–01, Available from Shinihon, Japan) was included at a dosage of 3,3 ml/kg feed.

The results, determined as the difference between the energy of the feed supplied and the energy of the voided excreta, is presented in Table 2, below.

TABLE 2

Apparant Metabolizable Energy (AMEn)

| Treatments | Dosage (ml/kg feed) | Number of animals (N) | AMEn (MJ/kgDM)/ improvement |
|---|---|---|---|
| Basal diet (B) | — | 125 | 12.17[bc] |
| B + lactase | 3.3 | 125 | 12.06[c]/−0.9% |
| B + galactanase | 6.7 | 125 | 12.37[abc]/+1.5% |
| B + lactase + galactanase | 3.3 + 6.7 | 125 | 12.68[a]/+3.9% |

Values with Different Subscripts are Significantly Different (P<0.05).

This illustrate that a galactanase of the invention is useful in the animal feed industry.

What is claimed is:

1. An isolated enzyme exhibiting galactanase activity selected from the group consisting of:
   (a) a polypeptide encoded by the DNA sequence present in plasmid pYES 2.0 present in *Escherichia coli* DSM 10355;
   (b) a polypeptide comprising an amino acid sequence of amino acid residues 19–342 of SEQ ID NO 2;
   (c) a polypeptide which has an amino acid sequence that is at least 70% homologous with one or both of polypeptides (a) and (b); and
   (d) a fragment of (a) or (b) which exhibits galactanase activity.

2. The enzyme of claim 1, which is obtained from a filamentous fungus, yeast, or bacteria.

3. The enzyme of claim 2, which is obtained from a strain of the family Polyporaceae.

4. The enzyme of claim 3, which is obtained from a strain of Meripilus, Bjerkandera, or Spongipellis.

5. The enzyme of claim 4, which is obtained from a strain of *Meripilus giganteus*.

6. The enzyme of claim 5, which is obtained from *Meripilus giganteus* CBS No. 521.95.

7. The enzyme of claim 1, which is obtained from a strain of an Aspergillus sp., Phytophthora sp., Talaromyces sp., Thermoascus sp., Sporotrichum sp., or Penicillium sp.

8. The enzyme of claims, which is obtained from *Escherichia coli* DSM No. 10355.

9. The enzyme of claim 1, which comprises an amino acid sequence of amino acid residues 19–342 of SEQ ID NO 2.

10. The enzyme of claim 1, which has an amino acid sequence that is at least 70% homologous with one or both of polypeptides (a) and (b).

11. The enzyme of claim 10, which has an amino acid sequence that is at least 80% homologous with one or both of polypeptides (a) and (b).

12. The enzyme of claim 11, which has an amino acid sequence that is at least 90% homologous with one or both of polypeptides (a) and (b).

13. The enzyme of claim 12, which has an amino acid sequence that is at least 95% homologous with one or both of polypeptides (a) and (b).

14. The enzyme of claim 13, which has an amino acid sequence that is at least 97% homologous with one or both of polypeptides (a) and (b).

15. The enzyme of claim 1, which has an amino acid sequence that differs from the amino acid sequence of amino acid residues 19–342 of SEQ ID NO 2 by no more than three amino acids.

16. The enzyme of claim 15, which has an amino acid sequence that differs from the amino acid sequence of amino acid residues 19–342 of SEQ ID NO 2 by no more than two amino acids.

17. The enzyme of claim 16, which has an amino acid sequence that differs from the amino acid sequence of amino acid residues 19–342 of SEQ ID NO 2 by one amino acid.

18. A composition comprising the enzyme of claim 1.

19. The composition of claim 18, further comprising an alpha-arabinosidase, alpha-glucuronisidase, arabinanase, beta-galactosidase, beta-xylosidase, glucanase, laccase, pectate lyase, pectin acetylesterase, pectin lyase, pectin methylesterase, phytase, polygalacturonase, rhamnogalacturonase, xylan acetyl esterase, or xylanase.

* * * * *

SEQUENCE LISTING

<160> NUMBER OF SEQ ID NOS: 2

<210> SEQ ID NO 1
<211> LENGTH: 1026
<212> TYPE: DNA
<213> ORGANISM: Meripilus giganteus
<220> FEATURE:
<221> NAME/KEY: CDS
<222> LOCATION: (1)...(1026)

<400> SEQUENCE: 1

```
atg atg ttc gtg ctc ccc ttc ctg ctg ctc tca ttc tcc tgg ctg gcg      48
Met Met Phe Val Leu Pro Phe Leu Leu Leu Ser Phe Ser Trp Leu Ala
 1               5                  10                  15 agc gcc ctg acg tac aag ggc gca gac atc tcc tcg gtc cct ctg gta      96
Ser Ala Leu Thr Tyr Lys Gly Ala Asp Ile Ser Ser Val Pro Leu Val
             20                  25                  30 gag cag gca ggc atc aag tac acg gac ggc gga aaa gtc acg ccc ttc     144
Glu Gln Ala Gly Ile Lys Tyr Thr Asp Gly Gly Lys Val Thr Pro Phe
         35                  40                  45 gag aac atc atc cac aac cac ggc gcg aac acc gtg cgc atc cgc att     192
Glu Asn Ile Ile His Asn His Gly Ala Asn Thr Val Arg Ile Arg Ile
     50                  55                  60 tgg acc gcg ggc gac tac aac ctg cag tat ggg ctg gcg ctc gcg aag     240
Trp Thr Ala Gly Asp Tyr Asn Leu Gln Tyr Gly Leu Ala Leu Ala Lys
 65                  70                  75                  80 cgg gtg aag gcg gcc ggc ctg acg ctg gtg gtc gac ctc cat tac agc     288
Arg Val Lys Ala Ala Gly Leu Thr Leu Val Val Asp Leu His Tyr Ser
                 85                  90                  95 gat aca tgg gcg gac ccc gga aaa cag gcg att ccc tcg gca tgg ccc     336
Asp Thr Trp Ala Asp Pro Gly Lys Gln Ala Ile Pro Ser Ala Trp Pro
            100                 105                 110 aag gac ttg gac gga ttg aac act cag att tgg cag tac acg aag gac     384
Lys Asp Leu Asp Gly Leu Asn Thr Gln Ile Trp Gln Tyr Thr Lys Asp
        115                 120                 125 gtt gtg acg agc ttc gca aac caa ggc acc cca att gac atc ctc cag     432
Val Val Thr Ser Phe Ala Asn Gln Gly Thr Pro Ile Asp Ile Leu Gln
    130                 135                 140 gtc ggc aac gag att aac aac gga ctc ctg tgg cct gtc gga gag atc     480
Val Gly Asn Glu Ile Asn Asn Gly Leu Leu Trp Pro Val Gly Glu Ile
145                 150                 155                 160 tcg tcc aat ggc atc aac ccc gtc tcg cag ctg ctc cat tcc gcc ata     528
Ser Ser Asn Gly Ile Asn Pro Val Ser Gln Leu Leu His Ser Ala Ile
                165                 170                 175
```

```
aac ggc gcc aaa gcg gca ggc aac ccg aag atc ctc atc cac ctc gcg      576
Asn Gly Ala Lys Ala Ala Gly Asn Pro Lys Ile Leu Ile His Leu Ala
            180                 185                 190 aac ggc tgg gac tgg tcc ggg ctc aac tcg ttc ttt ggc aag gtc ttc      624
Asn Gly Trp Asp Trp Ser Gly Leu Asn Ser Phe Phe Gly Lys Val Phe
            195                 200                 205 atc ccg ggc gcg ctc tcc gcc gac gag gtc gac atc atc ggc gta tcc      672
Ile Pro Gly Ala Leu Ser Ala Asp Glu Val Asp Ile Ile Gly Val Ser
    210                 215                 220 ttc tac ccg ttc tat gac gcc ggc gcg acg ctt tcc gcg ctc aag tca      720
Phe Tyr Pro Phe Tyr Asp Ala Gly Ala Thr Leu Ser Ala Leu Lys Ser
225                 230                 235                 240 tcg ctc gct aac ctc gcg aac acg ttc aag aag cct atc gtc gtc gcg      768
Ser Leu Ala Asn Leu Ala Asn Thr Phe Lys Lys Pro Ile Val Val Ala
            245                 250                 255 gag acg gat tgg ccc gtg gct tgc tca ggc gtg aag ttg acc gag ccg      816
Glu Thr Asp Trp Pro Val Ala Cys Ser Gly Val Lys Leu Thr Glu Pro
            260                 265                 270 agc gtc ccc gtc tcg acg agt gga cag cag aca tgg atc ggc gac atc      864
Ser Val Pro Val Ser Thr Ser Gly Gln Gln Thr Trp Ile Gly Asp Ile
            275                 280                 285 aag aac gtg ctg cag tcc ctc cct aac ggc ctc ggc caa ggt att ttc      912
Lys Asn Val Leu Gln Ser Leu Pro Asn Gly Leu Gly Gln Gly Ile Phe
            290                 295                 300 tac tgg gag cct ggt tgg atc ggc aac gcg aac ctc gga tcg gga tgt      960
Tyr Trp Glu Pro Gly Trp Ile Gly Asn Ala Asn Leu Gly Ser Gly Cys
305                 310                 315                 320 tcg gac aac ctc ctc gtt tct tcc aac gga gct act cgg gac tcg atc     1008
Ser Asp Asn Leu Leu Val Ser Ser Asn Gly Ala Thr Arg Asp Ser Ile
            325                 330                 335 aac atc ttc aac cag atg                                              1026
Asn Ile Phe Asn Gln Met
            340

<210> SEQ ID NO 2
<211> LENGTH: 342
<212> TYPE: PRT
<213> ORGANISM: Meripilus giganteus

<400> SEQUENCE: 2

Met Met Phe Val Leu Pro Phe Leu Leu Leu Ser Phe Ser Trp Leu Ala
 1               5                  10                  15

Ser Ala Leu Thr Tyr Lys Gly Ala Asp Ile Ser Ser Val Pro Leu Val
            20                  25                  30

Glu Gln Ala Gly Ile Lys Tyr Thr Asp Gly Gly Lys Val Thr Pro Phe
        35                  40                  45

Glu Asn Ile Ile His Asn His Gly Ala Asn Thr Val Arg Ile Arg Ile
    50                  55                  60

Trp Thr Ala Gly Asp Tyr Asn Leu Gln Tyr Gly Leu Ala Leu Ala Lys
65                  70                  75                  80

Arg Val Lys Ala Ala Gly Leu Thr Leu Val Asp Leu His Tyr Ser
                85                  90                  95

Asp Thr Trp Ala Asp Pro Gly Lys Gln Ala Ile Pro Ser Ala Trp Pro
            100                 105                 110

Lys Asp Leu Asp Gly Leu Asn Thr Gln Ile Trp Gln Tyr Thr Lys Asp
        115                 120                 125

Val Val Thr Ser Phe Ala Asn Gln Gly Thr Pro Ile Asp Ile Leu Gln
    130                 135                 140
```

-continued

```
Val Gly Asn Glu Ile Asn Asn Gly Leu Leu Trp Pro Val Gly Glu Ile
145                 150                 155                 160

Ser Ser Asn Gly Ile Asn Pro Val Ser Gln Leu Leu His Ser Ala Ile
                165                 170                 175

Asn Gly Ala Lys Ala Ala Gly Asn Pro Lys Ile Leu Ile His Leu Ala
            180                 185                 190

Asn Gly Trp Asp Trp Ser Gly Leu Asn Ser Phe Phe Gly Lys Val Phe
        195                 200                 205

Ile Pro Gly Ala Leu Ser Ala Asp Glu Val Asp Ile Ile Gly Val Ser
    210                 215                 220

Phe Tyr Pro Phe Tyr Asp Ala Gly Ala Thr Leu Ser Ala Leu Lys Ser
225                 230                 235                 240

Ser Leu Ala Asn Leu Ala Asn Thr Phe Lys Lys Pro Ile Val Val Ala
            245                 250                 255

Glu Thr Asp Trp Pro Val Ala Cys Ser Gly Val Lys Leu Thr Glu Pro
            260                 265                 270

Ser Val Pro Val Ser Thr Ser Gly Gln Gln Thr Trp Ile Gly Asp Ile
        275                 280                 285

Lys Asn Val Leu Gln Ser Leu Pro Asn Gly Leu Gly Gln Gly Ile Phe
    290                 295                 300

Tyr Trp Glu Pro Gly Trp Ile Gly Asn Ala Asn Leu Gly Ser Gly Cys
305                 310                 315                 320

Ser Asp Asn Leu Leu Val Ser Ser Asn Gly Ala Thr Arg Asp Ser Ile
            325                 330                 335

Asn Ile Phe Asn Gln Met
            340
```